(12) United States Patent
Ierulli (10) Patent No.: US 6,453,901 B1
(45) Date of Patent: Sep. 24, 2002

(54) NASAL DILATOR AND METHOD OF MAKING THE SAME

(76) Inventor: Joseph V. Ierulli, 3926 SW. Water Ave., Portland, OR (US) 97201

( * ) Notice: Subject to any disclaimer, the term of this patent is extended or adjusted under 35 U.S.C. 154(b) by 0 days.

(21) Appl. No.: 09/357,062

(22) Filed: Jul. 19, 1999

(51) Int. Cl.[7] .............................................. A61M 16/00
(52) U.S. Cl. .................. 128/200.24; 128/848; 606/191; 606/196; 606/199; 606/201; 606/204.45
(58) Field of Search ............................ 128/848, 200.24, 128/858; 606/199, 204.45, 191, 196, 201; 602/41, 61

(56) References Cited

U.S. PATENT DOCUMENTS

| | | | | |
|---|---|---|---|---|
| 5,611,333 A | * | 3/1997 | Johnson | 128/200.24 |
| 5,653,224 A | * | 8/1997 | Johnson | 128/200.24 |
| 5,842,469 A | * | 12/1998 | Rapp et al. | 128/200.24 |
| 5,890,486 A | * | 4/1999 | Mitra et al. | 128/200.24 |
| 5,957,126 A | * | 9/1999 | Neeser | 128/200.24 |
| 6,058,931 A | * | 5/2000 | Muchin | 128/200.24 |
| 6,065,470 A | * | 5/2000 | Van Cromvoirt et al. | 128/200.24 |
| 6,080,179 A | * | 6/2000 | Gould | 606/204.45 |
| 6,098,616 A | * | 8/2000 | Lundy, Jr. et al. | 128/200.24 |

* cited by examiner

*Primary Examiner*—Aaron J. Lewis
*Assistant Examiner*—Mital Pital
(74) *Attorney, Agent, or Firm*—Olson & Olson

(57) ABSTRACT

The nasal dilator of this invention comprises a truss which includes a resilient spring member secured between a base layer and a cover member. The cover member extends beyond the perimeter of the spring member for maximum adherence of the truss to the outer skin surface of the nose of a wearer. The lateral sides of the dilator are angled to correspond to the line where the nose meets the cheek, and a separation, projection, or other index marker is formed member midway between the end edges of the truss, to assist centering the dilator on the nose. In one embodiment the spring member is formed with end pairs of resilient spring fingers configured to provide dilating force to the vestibule area of the nose, in addition to the valve area. The dilator construction allows mass production on a continuous basis by forming continuous, web-connected spring members laminated between continuous strips of flexible base layer and cover member material, and then cutting through the laminate along lines defining the outer periphery of the dilator.

40 Claims, 5 Drawing Sheets

NASAL DILATOR AND METHOD OF MAKING THE SAME

BACKGROUND OF THE INVENTION

This invention relates to devices for dilating human tissue, and more specifically to a novel nasal dilator construction of improved performance.

Nasal dilators are well known, and are generally of the internal or external variety. Internal nasal dilators are placed inside the interior of the nose and act to urge the nostril wall tissues outward, to enhance breathing. This type of nasal dilator is both uncomfortable and obtrusive. Their very presence inside the nose increases resistance to airflow, thereby at least in part defeating the intended purpose of increasing airflow within the nasal passageways.

External nasal dilators typically use a flat, semi-rigid spring member flexed across and extending on each side of the bridge of the nose adjacent the nasal valve. That portion of an external nasal dilator which extends across the bridge of the nose is generally the intermediate segment, and those portions which engage the nasal outer wall tissues adjacent the first and second nasal passageways on each side of the bridge are generally the first and second end regions, which are thus interconnected by the intermediate segment. The inherent force of the flexed spring member, held to the skin of the nose by the adhesive, lifts the outer wall tissues of the nostrils and dilates the nasal passageways, reducing the resistance to airflow and correspondingly increasing airflow through the nasal passageways during breathing. The spring members of current well known external nasal dilators are about 4.6 to 6.1 cm (1.80" to 2.40") long, approximately 0.5 cm (0.20") wide, and are typically 0.010" thick, so as to allow the dilator to exert a spring return dilating force of about 25 grams. This amount of spring return is considered ideal for general use. Departing significantly from the aforementioned dimensions would render the spring return force outside the desired limits of between 15 and 35 grams. Less than 15 grams of spring return force may not be enough dilation for many users, while a spring return force of greater than 35 grams may be uncomfortable for many users. The preferred spring member material as defined in the art is a biaxially oriented polyester resin. This material is widely available in standard thicknesses of 0.005", 0.007", and 0.010".

External dilators are, of necessity, releasably secured to the skin of the nose by use of pressure sensitive adhesives. However, external nasal dilators also have an inherent problem of maintaining adhesion to the skin for extended periods, primarily at the end regions of the device, due to the constant return force of the spring member acting on the releasable adhesive. Use of stronger adhesives that would maintain adhesion to the skin under all conditions, is undesirable because such adhesives are likely to damage the skin upon removal of the dilator.

U.S. Pat. No. 1,292,083 discloses an external nasal dilator which employs two discreet adhesive pads connected one each to opposite ends of a spring member. The adhesive pads engage the outer wall tissues of the first and second nasal passages, effectively dilating them. Each terminal end of the spring member is attached centrally to each pad, which evenly distributes the delaminating force of the spring member in a radius extending around the terminal end. While this arrangement is effective in maintaining adhesion of the device end regions to the nose, it cannot be mass produced on an economical basis.

Spanish Utility Model No. 289,561 and U.S. Pat. No. 5,546,929 each discloses a nasal dilator which uses a spring member centrally located on an adhesive pad. The adhesive pad extends around the spring member on all sides, extending well past each terminal end thereof. This arrangement adequately maintains adhesion of the device end regions to the nose, but the requirement of centrally located spring member renders these devices difficult to mass produce.

U.S. Pat. No. 5,533,503 discloses a nasal dilator which uses two narrow resilient bands, each approximately 0.80" to 0.135" wide and 0.010" thick. The two bands combined provide a spring return force of approximately 26 grams. This dilator is produced in a continuous manufacturing process from a continuous laminate of several materials. To accomplish the continuous process, adhesive material for engaging the nose which would otherwise extend immediately beyond the terminal ends of the spring members is omitted in lieu of a complicated end region structure which requires extensions separated from protrusions by back cuts (or other discontinuity of material), said protrusions in turn separated by a valley. The back cuts redirect the delamination forces exerted by the spring members from primarily peel forces into primarily sheer forces. All of these elements must be present, and must work in concert, in order to maintain adequate adhesion of the end regions to the sides of the nose. This complex structure also requires the two parallel resilient bands to be in very close proximity to each other. As a result of the aforementioned requirements, this device is difficult to accurately mass produce.

U.S. Pat. No. 5,611,333 discloses a nasal dilator which employs various relief cuts, notches or other removal of material from within the perimeter of the spring member, primarily at the end regions of the spring member, in order to reduce the spring return force sufficiently so as to maintain adhesion of the device to the skin of the nose. The removal of material during manufacturing renders the device problematic for mass production on an economic basis.

Nasal dilators provided heretofore address only that area of the nasal passageways in the immediate vicinity of the nasal valve, while ignoring the vestibule area located immediately beyond the nostril openings and extending to the nasal valve.

U.S. Pat. No. 5,669,377 discloses a device which pulls upward on the tip of the nose and purportedly affects the vestibule area to aid nasal breathing. However, users may not readily accept, even in the privacy of their homes, wearing such a device which distorts the shape of the nose. Additionally, this device has no dilating effect on the nasal passage areas located above the vestibule.

External nasal dilators are meant to be centered horizontally across the bridge of the nose, so that the dilating force is evenly distributed across the first and second nasal passages. Nasal dilators provided heretofore lack a means for aiding the end user in precise alignment of the dilator with the bridge of the nose.

The Clear Passage nasal strip distributed by Schering Plough and marketed under the Afrin brand label is asymmetric. Its length is curved arcuately, and it has a wide protrusion of material along the apex of the curve. To aid end users in applying the dilator, the marketing and labelling of this device illustrates that the protrusion of material is meant to be placed up, so that the curved length of the device extends the end regions downward over the first and second nasal passages. However, this construction does little to aid the user in precise alignment of the dilator with the bridge of the nose.

Spanish Utility Model 289,561 FIGS. 1d and 2d also illustrate a protrusion of material extending upward from the device center. However, the protrusion also extends horizontally at least partway on each side of the bridge of the nose, and thus does not aid the user in precise horizontal alignment of the dilator to the nose.

Most medical devices which are adhered to or otherwise engage the skin, including those devices noted above, provide in their structure a layer of soft, absorbant material interposed between all or part of the device and the skin, for the purpose of making the device comfortable to use and wear. In some cases the material may include features which allow it to aid in device function, or aid in interfacing the device with the skin. However, use of a material layer for the purpose of user comfort has long been commonplace throughout medical device art.

Clearly, there is a continuing need for a nasal dilator that is effective in dilating the nasal passages of the nose, that is inexpensively manufactured in a continuous process, which maintains adequate adhesion at the end regions without use of complicated structures, which addresses multiple areas of the nasal passages, which aids the user in precise alignment of the dilator upon the nose, and which is comfortable to use and wear.

SUMMARY OF THE INVENTION

The nasal dilator of this invention comprises a truss having first and second end regions for engaging the nose on each side of the bridge adjacent the first and second nasal passages, and an intermediate segment interconnecting said first and second end regions. The truss width is centered adjacent the nasal valve area and may extend vertically in one or both directions therefrom. The truss is adapted for a method of continuous manufacture, and further adapted to assist precise horizontal placement of the dilator onto the nose by the user. Resilient means extends along the truss, and when applied to the nose, acts to stabilize and dilate the nasal passages. The resilient means includes a resilient spring member, or members, which may be of a variety of lengths, widths and thicknesses, and which may include extensions, or resilient spring fingers. The dilator and/or its components may have a number of peripheral geometries for engaging multiple areas of the outer wall tissues of the nasal passages simultaneously, and for directing and/or varying the amount of dilating force exerted upon those areas of the outer wall tissues so engaged. The truss includes a flexible cover material that defines the overall shape of the dilator. The truss further includes a soft, absorbant, base material layer interposed between at least a portion of the truss and the nasal outer wall tissues engaged by the truss, for the purpose of user comfort. The truss may also include a relief cut adjacent each terminal end of the spring member for redirecting the spring return peel forces into sheer forces. The truss, or its components, may be angled at their end edges to correspond to the line where each side of the nose meets each cheek.

It is the principal objective of this invention to provide a nasal dilator which overcomes the aforementioned limitations and disadvantages of prior nostril dilators.

Another objective of this invention is the provision of a nasal dilator of the class described which is capable of mass production in large numbers at economical cost.

Another objective of this invention is the provision of a nasal dilator of the class described which may be configured to redirect the spring return force at the device and regions from primarily peel forces into primarily shear forces.

A further objective of this invention is to provide a nasal dilator off the class described that incorporates in its method of manufacture means by which to facilitate the centering of the dilator accurately on the nose.

Still another objective of this invention is the provision of a nasal dilator of the class described that may be configured to effect selected dilation of various segments of the nasal passageways.

A still further objective of this invention is to provide a nasal dilator of the class described which is configured, when attached to the nose of a wearer, to terminate at its end edges along the line separating the nose from the cheek.

The foregoing and other objects and advantages of this invention will appear from the following detailed description, taken in connection with the accompanying drawings of preferred embodiments.

DESCRIPTION OF THE PREFERRED EMBODIMENTS

Figure 1:
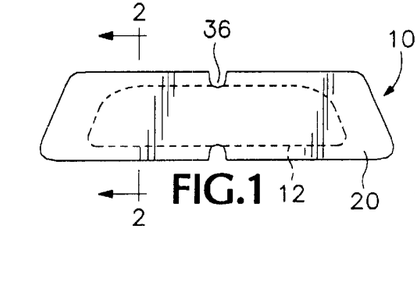
FIG. 1 is a plan view of a nasal dilator embodying the features of this invention.
Figure 2:
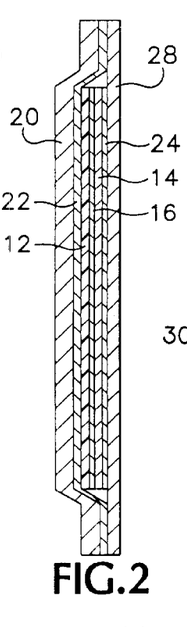
FIG. 2 is a sectional view, on an enlarged scale, taken on the line 2—2 in FIG. 1.
Figure 3:
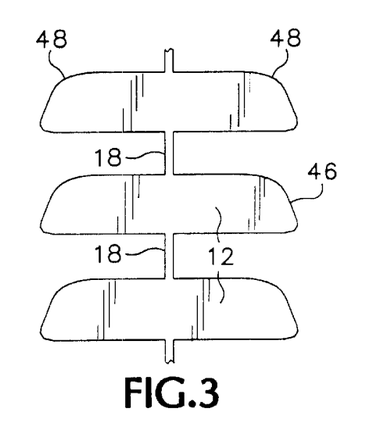
FIG. 3 is a fragmentary plan view illustrating a method of making the spring member of the nasal dilator of FIG. 1.

The embodiment illustrated in FIGS. 1–7 shows a nasal dilator 10 construction that affords production on a large scale. The construction comprises a truss, which includes a resilient spring member component 12 made of synthetic resin, preferably a biaxially oriented polyester film. FIG. 3 shows a plurality of spring member components produced from an elongated or continuous sheet of such resin. The plurality of spring members are interconnected midway between their ends by webs 18 that integrate them into a continuous strip. The strip is cut to the shape illustrated by a continuous cutting process.

Figure 4:
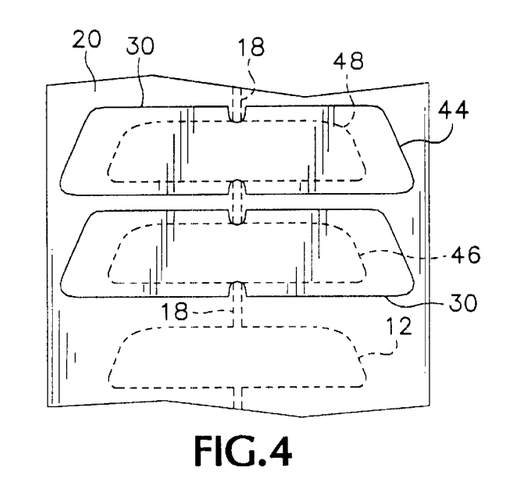
FIG. 4 is a fragmentary plan view illustrating a method of assembling the continuous material laminate used in the manufacture of the nasal dilator of FIG. 1 for subsequent processing into finished dilator units.

In FIG. 4 the spring member strip is laminated to an elongated or continuous strip of flexible cover material 20. The cover material may be made of any suitable fabric or plastic film material, but is preferably made of a thin, lightweight, nonwoven fabric. A layer of pressure sensitive adhesive 22 on one side of cover material 20 joins the strip of spring members and cover material into a one-piece, laminated assembly.

In addition, the elongated or continuous sheet of synthetic resin may be laminated to an elongated or continuous strip of base material 14, by a layer of adhesive 16, prior to the continuous cutting process. As with cover material 20, base material 14 may be made of any suitable fabric or plastic film material, but is preferably made of a thin, lightweight, nonwoven fabric. The result is a plurality of spring members, cut to the shape shown in FIG. 3, which include a base layer 14 for interfacing comfortably with the skin. The use of such an interface is usual and customary in those medical devices which either engage or adhere to the skin.

Figure 7:
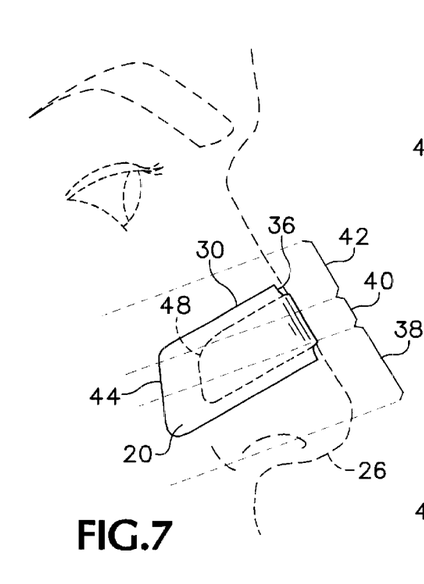
FIG. 7 is a side elevation showing the attachment of the nasal dilator of FIG. 1 to the nose of a wearer, depicted in broken lines, and showing in broken lines the approximate segments of the nasal passageways.

As seen in FIG. 2, a layer of pressure sensitive adhesive 24 covers the outer side of the base layer component 14, and together with adhesive 22 on cover member component 20 extending around and beyond base layer 14, provides for securing the unit removably to the outer surface of the nose 26 (FIG. 7). A layer of a pair of flexible, adhesive protection release line components 28 removably covers the adhesive layer 24 and the exposed areas of adhesive 22 preliminary to use of the nasal dilator unit 10.

Alternatively, said strip of spring members may be laminated simultaneously in between elongated or continuous strips of both base material 14 and cover material 20. The result produces dilator 10, as described in the following paragraph, in which base layer 14 and cover member 20 are of the same dimension and configuration.

The one-piece, laminated assembly of FIG. 4 is cut into individual units of complete nasal dilators 10 by cutting through the assembly along lines 30 which determine the peripheral shape of the dilator units. The cuts extend through the material, outwardly of spring member 12, to produce dilators 10 that include the release liner 28, allowing the dilators to be packaged individually. Alternatively, the cuts may extend only to the release liner layer 28 by the well known kiss-cut technique. This arrangement allows the dilators 10 to be packaged in rolls or in flat sheets of a plurality of dilators 10 secured to the single release liner.

Figure 5:
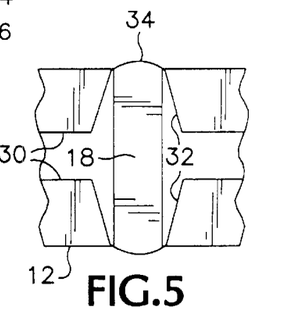
FIG. 5 is a fragmentary plan view, on an enlarged scale, illustrating the method of severing the units of the assembly of FIG. 4.
Figure 6:
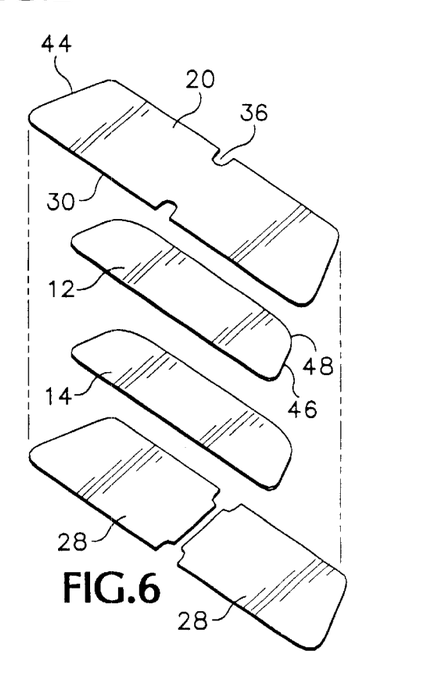
FIG. 6 is an exploded view of the components of the nasal dilator of FIG. 1.

As seen in FIG. 5, cut lines 30 converge inwardly at 32 along opposite sides of the web 18 and then sever web 18 by an arcuate cut line 34. The line 34 may extend slightly into the lateral margins of the spring member 12, to insure against the formation of sharp corners.

Cut lines 32 thus create separations 36 of material at the center of the upper and lower transverse cut lines 30. These material separations may be formed as a notch, v-cut, slot, or the like. When dilator 10 is applied to the nose, separations 36 are meant to be aligned vertically with the center line of the bridge of the nose, this aiding the user in precise horizontal placement of the dilator to the nose. Alternatively, one or more material separations may be made within the periphery of the truss, and need not extend through all layers of the truss, so long as they are visible, and allow the user to align the lateral center of dilator 10 with the center line of the bridge of the nose.

To assist in the understanding of the various parts of the nasal passageways discussed herein, FIG. 7 illustrates, by broken lines, the approximate area 38 of the nasal vestibule, the approximate area 40 of the nasal valve, and the approximate area 42 above the nasal valve area. The embodiments of this invention are designed to register one or more components of the truss with the outer wall tissues of selected areas of the nasal passageways, and to direct variable dilating forces to those areas.

As further seen in FIG. 7, lateral end edges 44 of the cover member 20 are angled upwardly and inwardly to correspond to the line where the nose meets the cheek. This provides maximum adhesion of the dilator to the side areas of the nose, for corresponding maximum dilation of the nasal passageways.

In using the nasal dilator 10, the release liner 28 is removed and the dilator is applied over the nose 26 by aligning the separations 36 with the longitudinal line of the bridge of the nose, and then pressing the dilator against the skin along the opposite sides of the bridge.

Upon release of hand pressure against the dilator, the resilient spring member 12 moves inherently to straighten, exerting a spring return force which, due to its adherence to the nose, stabilizes and dilates the nasal outer wall tissues. The spring return acts on all components of the dilator, which in turn act on the nasal wall tissues, and lessens gradiently between the periphery of the spring member and the outer edges of the cover member. The spring return force can continue beyond the outer edges of the cover member, depending upon the amoung of spring return generated by the dilator 10 being flexed across the nose. Thus the peripheral geometry of the truss member and/or its components, together with the amount of spring return generated by the spring member, determine the extent of nasal outer wall surface area affected by dilator 10.

The dilator 10 includes a spring member 12 that is approximately 1.2 cm (0.47") wide and 0.007" thick. The thickness preferably corresponds to from 1% to 2% of the spring member width in order to arrive at a spring return force of from 20 to 30 grams. As illustrated in FIG. 7, the dilator is positioned so that the width of the spring member extends into the vestibule area 38 as well as into the nasal valve area 40.

The angled outside edges 46 of spring member 12 allow it to conform to the shape of cover member 20. The resulting shorter length of the upper half of the spring member combined with the narrowing width at the upper half of the bridge of the nose creates a higher spring return force along the upper long edge of dilator 10. To compensate, upper outside corners 48 of spring member 12 may be rounded or tapered so as to gradiently reduce the approximate width of the spring member at each end, which creates a lessensing of the spring return force thereabout.

Figure 8:
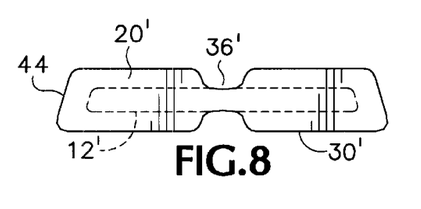
FIG. 8 is a plan view of a second form of nasal dilator embodying the features of this invention.

FIG. 8 illustrates a modification of the dilator of FIG. 1 in which the spring member 12' is approximately 0.19" wide and 0.010" thick, thus of less width and greater thickness than spring member 12 in order to arrive at a spring return force of approximately 25 grams. Base layer 14' and cover member 20' are also of reduced width, to direct dilation to primarily the nasal valve area, and to accommodate use on noses of smaller size. The separations 36' allow the continuous manufacturing process of FIG. 4 while also facilitating precise horizontal alignment on the nose of the wearer.

Figure 9:
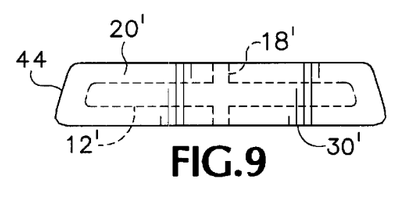
FIG. 9 is a plan view of a third form of nasal dilator embodying the features of this invention.

FIG. 9 differs from FIG. 8 in that webs 18' are terminated at the cut lies 30' of cover member 20' during the continuous manufacturing process. This allows the continuous manufacturing process to operate at a faster rate, at the expense of separations 36' shown in FIG. 8. Base layer 14' may be of the same configuration and dimension as spring member 12' or cover member 20'.

Figures 10, 11:
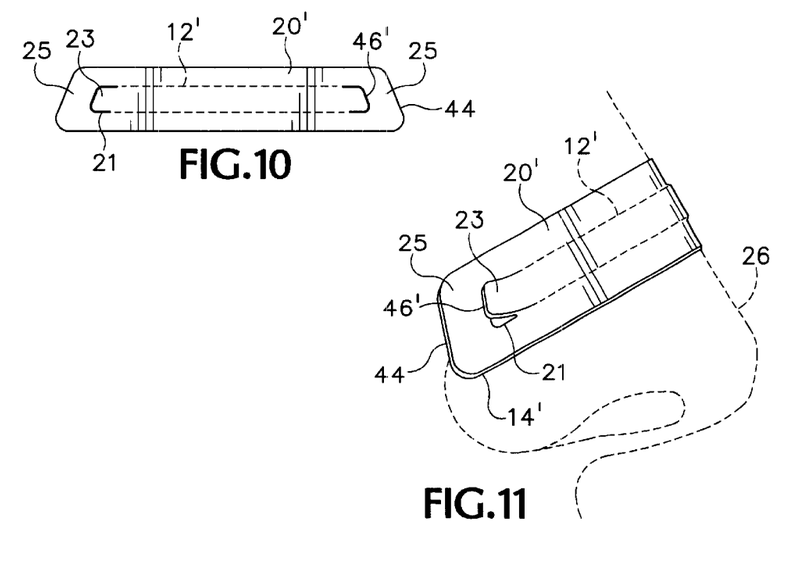
FIG. 10 is a plan view of a fourth form of nasal dilator embodying the features of this invention.
FIG. 11 is an enlarged side elevation of the dilator of FIG. 10 in use on the nose of a wearer.

To further aid adhesion of the end regions of the truss member to the skin of the nose of a wearer, the dilator of FIG. 10 includes relief cuts 21 in cover member 20' located adjacent and outward of each terminal end of spring member 12'. The cuts extend through at least the cover member 20', and otherwise extend through the truss member. The relief cuts correspond to the general outline 46' of the terminal ends of the spring member, and the ends of the cuts may extend toward the center portion of the spring member along the upper and lower longitudinal edges of the spring member. The cuts are positioned entirely within the periphery of the truss member, as close as practicable to the spring member, without coming into contact with the spring member.

As seen in FIG. 11, the relief cuts 21 cause each spring member end 23 to separate from the surrounding end portion 25 of the truss member. While this separation may reduce nasal dilation locally, it has the advantage of redirecting or transforming the delaminating spring return force at the truss member end regions from primarily peel forces into primarily sheer forces. Shear forces are better withstood by the adhesives typically used in base layer 14' and cover member 20' than are peel forces. The end portions 25 of the truss member, extending outward from the relief cuts to the surrounding peripheral edges of the truss member thereabout, provide a large, continuous surface area of adhesive contact with the skin, comprising the entire width of the cover member 20'. Thus, end portions 25 each serve as a substantial anchor by which the end regions of the truss member may withstand more easily the spring return force exerted by the flexed spring member when the dilator is in use on the nose of a wearer. The relief cuts create the added feature that the separated spring member ends may be easily grasped by the user to facilitate removal of the device after use.

Figure 12:
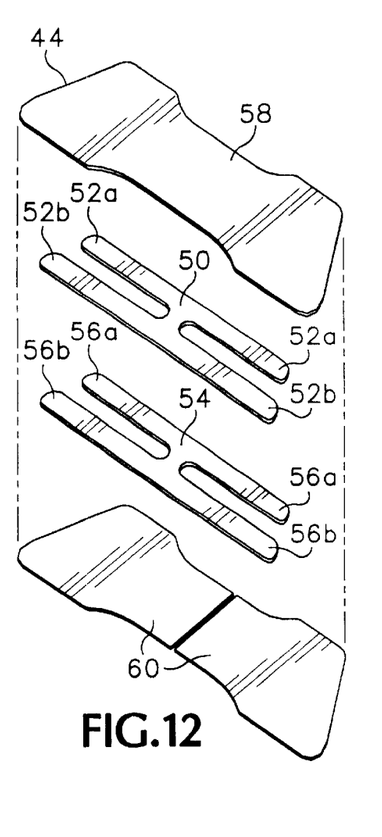
FIG. 12 is an exploded view of the components of a fifth form of nasal dilator embodying the features of this invention.
Figure 13:
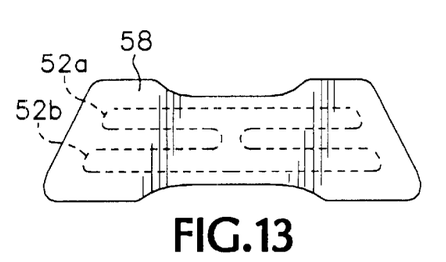
FIG. 13 is a plan view of a nasal dilator produced by the assembly of components of FIG. 12.

FIGS. 12 and 13 illustrate another form of nasal dilator in which the spring member 50 is slotted inwardly from both lateral ends, terminating short of the central portion. The slots effect bifurcation of the opposite end regions of the spring member to produce upper and lower pairs of resilient fingers 52a and 52b. The spring fingers are shown in FIGS. 10 and 11 as symetric about a common center of spring member 50. To meet specific needs of an individual, each spring finger may be of different lengths and widths, so as to affect the amount of localized spring return force about the nasal passages. For mass production however, the upper pair of fingers 52a are preferably of like dimension, so as to direct a balanced application of spring return force on each side of the bridge of the nose. The lower pair of fingers 52b are also preferably of like dimension, but with a combined length greater than spring fingers 52a. The width of the slots may be varied depending upon the length of the nose to be engaged by dilator 10, and to otherwise allow positioning of the dilator on the nose to affect a greater portion of either the nasal vestibule or the nasal valve areas of the nasal passageways. The base layer 54 preferably is formed with the corresponding pairs of spring fingers 56a and 56b, and the cover member 58 is dimensioned to extend over and beyond the length and width of the spring member 50. A pair of release liner sections 60 serve to protect the adhesive layer on the side of base layer 54 opposite the spring member 50 and the adhesive layer on the inner side of the cover member 58 outward of the margins of the bifurcated spring member 50.

Figure 14:
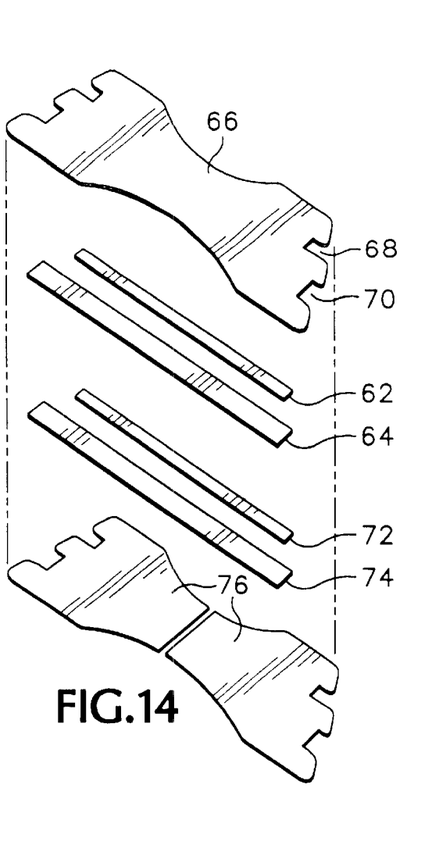
FIG. 14 is an exploded view of the components of a sixth form of dilator embodying the features of this invention.
Figure 15:
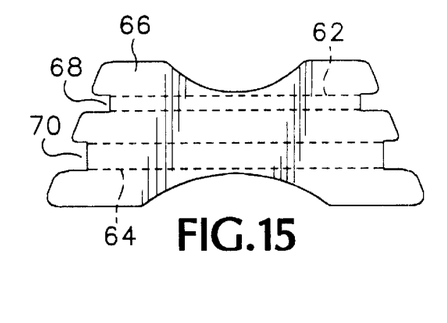
FIG. 15 is a plan view of the nasal dilator produced by the assembly of components of FIG. 14.

FIGS. 14 and 15 illustrate a variation of the embodiment of FIGS. 10 and 11, in providing a pair of spaced apart spring members 62 and 64 which may be of different lengths and widths, as well as of different thicknesses, so as to direct and apply diverse spring return forces to the nasal passages. The cover member 66 is configured with end notches 68 and 70 which align with the spring members 62 and 64 respectively, and register with the terminal ends of the spring members. The cover member further includes three pairs of tab extensions which extend past the terminal ends of spring members 62 and 64. The width of the middle pair of tab extensions defines the spaced apart relationship of spring members 62 and 64. As with FIGS. 10 and 11, the distance by which the spring members are spaced apart may be varied depending upon the length of the nose to be engaged by dilator 10, and otherwise allow positioning of the dilator on the nose to affect either a greater portion of the nasal vestibule or the nasal valve areas. However, the spring members must be spaced apart enough so that the middle tab extensions are of sufficient size so as to maintain adequate adhesion to the skin thereabout. The cover member 66 is further angled inward from bottom to top along portions of the end edges which define the terminal ends of the tab extensions, in the same manner as the end edges 44 in FIGS. 1, 8, 9, 11 and 13, to correspond to the line where the nose meets the cheek. Base layers 72 and 74 may be of the same dimensions as the spring members 62 and 64 respectively, or in the alternative, may be of the same dimensions as the cover member 66. In either case, the dilator may be manufactured in a continuous process similar to that illustrated in FIG. 4. Release liner sections 76 match the peripheral shape of cover member 66.

Figures 16, 17, 18, 19:
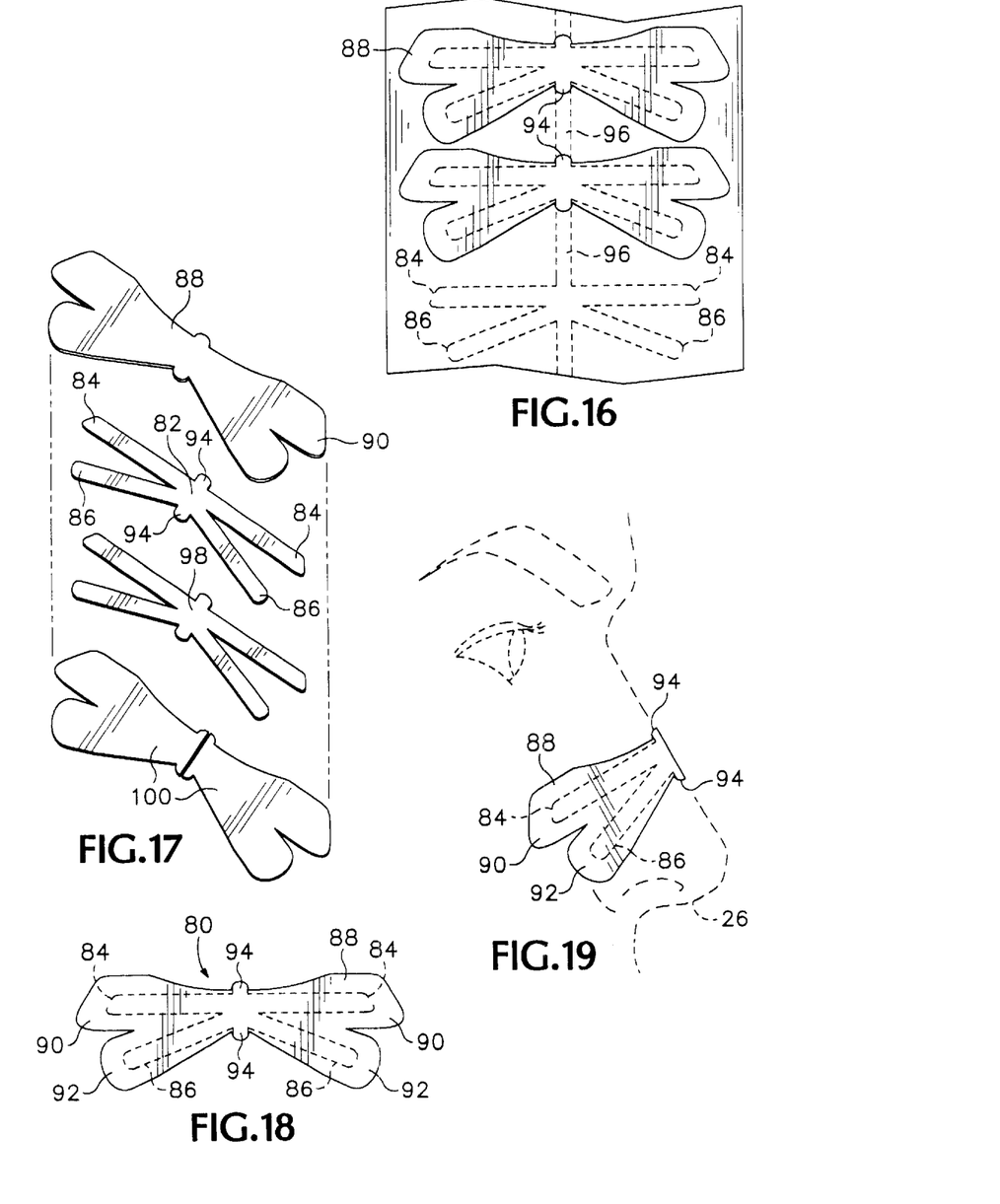
FIG. 16 is a fragmentary plan view illustrating a method of assembling the continuous material laminate used in the manufacture of a seventh form of nasal dilator for subsequent processing to finished dilator units.
FIG. 17 is an exploded view of the components of the seventh form of nasal dilator shown in FIG. 16.
FIG. 18 is a plan view of a nasal dilator produced by the assembly of components of FIG. 17.
FIG. 19 is a side elevation showing the attachment of the nostril dilator of FIG. 18 to the nose of a wearer, depicted in broken lines.

In FIGS. 16–18, the embodiment of dilator 60 includes a spring member 82 configured with pairs of spring fingers 84 and 86 which diverge symmetrically outward from a common center of spring member 82. To meet specific needs of an individual, each spring finger may diverge asymmetrically, or be of a different length and width, so as to affect the amoung of localized spring return force about the nasal passages. For mass production however, the pairs of fingers are preferably symmetric and of like dimension, so as to direct a balanced application of spring return force on each side of the bridge of the nose. The pair of fingers 84 preferably are situated in a straight line along the length of the truss adjacent the nasal valve area. Fingers 86 are angled sharply downward from the center of spring member 82, so as to extend over the nasal vestibule area.

Spring member 82 may be of a suitable thickness so as to arrive, in combination with the length and width of the spring fingers, at a desired spring return force for dilator 80. The cover member 88 is formed with separated end portions 90 and 92 which are configured to register with the diverging pairs of fingers 84 and 86, respectively, at the first and second end regions of the truss member. As shown in FIG. 19, end portions 90 are arranged to engage the nasal outer wall tissues adjacent the nasal valve area and end portions 92 are arranged to engage the nasal outer wall tissues adjacent the vestibule area. The separation 91 between end portions 90 and 92 generally conforms to the flare of the nostril, and allows the spring finger pairs to function somewhat independently from each other, to the extent allowed by the separation, and otherwise depending upon the degree to which said separation extends into the intermediate segment of the truss.

The center portion of the spring member 82 is formed with projections 94, by the selective severing of the web 96 between adjacent spring members 82 during the continuous manufacturing process shown in FIG. 16. The selective severing in this arcuate fashion serves to prevent the formation of sharp corners, and the resulting projections 94 serve to assist centering the dilator 80 on the nose, as explained hereinbefore with regard to the separations 36.

The base layer 98 may be configured to match either the shape of the spring member 82, or the cover member 88. The release liner sections 100 are configured to match the shape of the cover member 88 to protect the adhesive layer on the underside of the cover member, as well as the underside of the base layer 98.

Figure 20:
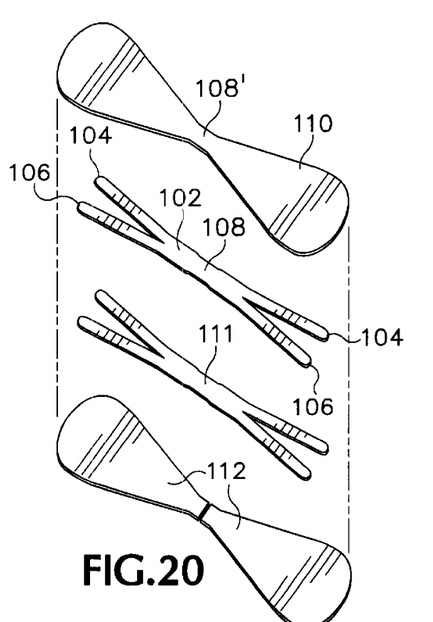
FIG. 20 is an exploded view of the components of an eighth form of nasal dilator embodying the features of this invention.
Figure 21:
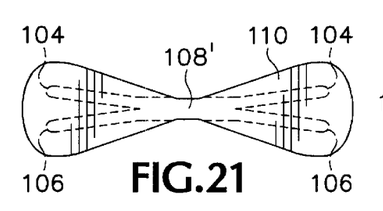
FIG. 21 is a plan view of the nasal dilator produced by the assembly of components of FIG. 20.

The embodiment shown in FIGS. 20 and 21 provides a spring member 102 like that of FIG. 8, but with end portions which bifurcate into pairs of fingers 104 and 106. The pairs of fingers diverge angularly from the long axis of the central portion 108. Unlike spring members 12 and 12', whose widths are constant from end to end, spring member 102 diverges into pairs of spring fingers substantially at the first and second end regions of the truss, allowing the spring return force to widen thereabout. Spring member 102 may be of a suitable thickness so as to arrive at a desired spring return force for the dilator. The cover member 110 diverges from the central portion 108' which matches the central portion 108 of the spring member 102, and extends around and beyond spring member 102, terminating in rounded outer end edges. The cover member is not separated at its end regions thereby allowing the spring fingers of each pair to function in concert. The base layer 110 may match the shape of either the spring member 102 or the cover member 110, and the release liner sections 112 match the shape of the cover member 110. This embodiment may be manufactured in a continuous process as illustrated in FIG. 4.

Figure 22:
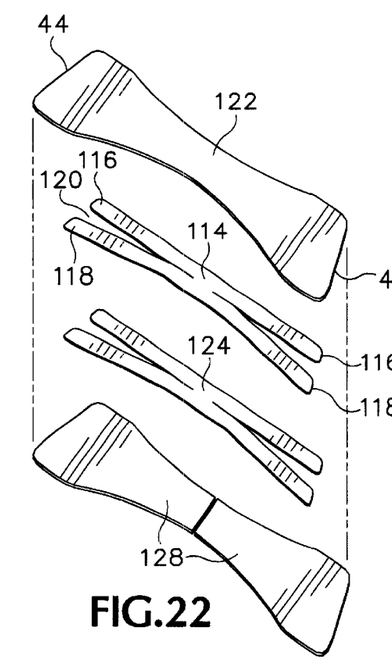
FIG. 22 is an exploded view of the components of a ninth form of nasal dilator embodying the features of this invention.
Figure 23:
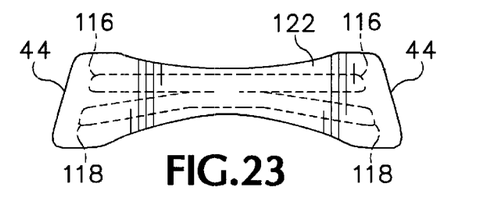
FIG. 23 is a plan view of the nasal dilator produced by the assembly of components of FIG. 22.

In the embodiment of FIGS. 22 and 23, the spring member 114 is configured with upper spring fingers 116 and lower spring fingers 118. The fingers 116 extend in a straight line, while fingers 118 diverge angularly downward therefrom and are slightly longer. The fingers are further separated by slits 120 which extend substantially into the center portion of spring member 114. The slits allow the upper and lower fingers to function in effect as two individual spring members oriented in close parallel proximity along the long edges of their center portions, but without incurring the difficulty of registering two separate components in such close proximity during the manufacturing process. The spring fingers thus exert a dilating force on a larger vertical area of the nasal passageways substantially at the device end regions. The cover member is not separated at its end regions, thereby allowing the spring fingers of each pair to function in concert. As explained hereinbefore, the dilator may thus be vertically aligned as the user prefers. The cover member 122 has angled outer end edges 44 to correspond to the line where the nose meets the cheek, and the terminal ends of the spring fingers are spaced the same distance from the end edges of the cover member. The base layer 124 preferably matches the shape of the spring member 114 and the release liner 126 matches the shape of the cover member 122.

From the foregoing it will be apparent that this invention provides a nasal dilator configuration adapted for use with noses of various sizes and of varying breathing requirements. Thus, the dilator may be configured to exert dilation force over greater or lesser areas of the outer wall tissues of the nasal passageways.

It will be apparent to those skilled in the art that many of the features of the various embodiments may be interchanged or used in combination with one another. It will be further apparent to those skilled in the art that various changes may be made in the size, shape, type, number and arrangement of parts described hereinbefore, without departing from the spirit of this invention and the scope of the appended claims.

I claim:

1. A nasal dilator, comprising:

a) a truss member having first and second end regions having a width and adapted to engage the outer wall tissues of the first and second nasal passages, b) an intermediate segment having a width and interconnection the first and second end regions, and configured to traverse the bridge of the nose located between the first and second nasal passages, c) resilient means extending along the truss member, including a resilient spring member secured on one side to at least a portion of the first and second end regions and the intermediate segment, the resilient spring member having a single thickness of from 1% to 2% of its width, said width being reduced gradiently to the outer ends thereof, d) adhesive means at the first and second end regions and the intermediate segment for removably engaging the dilator to the nose of a wearer, and e) a flexible cover member having one side secured to one side of the resilient spring member and extending outwardly beyond at least portions of the resilient spring member.

2. The nasal dilator of claim 1 including a flexible base layer having one side secured to the side of the resilient spring member opposite the side secured to the at least a portion of the first and second end regions.

3. The nasal dilator of claim 1 wherein at least one component of the truss member has at least portions of its end edges angled inward from bottom to top in a continuous line corresponding to a line where the nose meets the cheek.

4. The nasal dilator of claim 1 wherein the resilient spring member is bifurcated laterally to form resilient spring fingers extending into the first and second end regions of the truss member.

5. The nasal dilator of claim 1 wherein the resilient spring member has a thickness of about 0.007" and a width of about 0.47".

6. The nasal dilator of claim 1 wherein the resilient spring member has a thickness of about 0.010" and a width of about 0.19".

7. The nasal dilator of claim 1 including indicator means at the intermediate segment midway between the first and second end regions of the truss member for alignment with the bridge of the nose of a wearer for centering the dilator across the nose.

8. A nasal dilator for engaging the outer wall tissues of the nasal passages, comprising a truss member, including:
   a) first and second end regions adapted to engage the outer wall tissues of the first and second nasal passages,
   b) an intermediate segment interconnecting the first and second end regions, and configured to traverse the bridge of the nose located between the first and second
   c) resilient means extending along the truss member, including a resilient spring member having outer ends and secured to at least a portion of the first and second end regions and the intermediate segment,
   d) adhesive means at the first and second end regions and the intermediate segments for removably engaging the dilator to the nose of a wearer,
   e) a flexible cover member having one side secured to one side of the resilient spring member and extending outwardly beyond the outer ends of the resilient spring member, and,
   f) means for redirecting spring return force at the first and second end regions of the truss member from primarily peel forces into primarily shear forces, said redirecting means comprising relief cuts through the cover member located adjacent and outward of each terminal end of the spring member within the periphery of the truss member.

9. The nasal dilator of claim 8 including a flexible base layer having one side secured to the side of the resilient spring member opposite the side secured to the at least a portion of the first and second end regions.

10. The nasal dilator of claim 8 wherein the lateral end edges of the truss member are angled inward from bottom to top in a continuous line, corresponding to a line where the nose meets the cheek.

11. The nasal dilator of claim 8 wherein the resilient spring member is bifurcated laterally to form resilient spring fingers extending into the first and second end regions of the truss member.

12. The nasal dilator of claim 8 including indicator means at the intermediate segment midway between the first and second end regions of the truss member for alignment with the bridge of the nose of a wearer for centering the dilator across the nose.

13. A nasal dilator, comprising a truss member, including:
   a) first and second end regions adapted to engage the outer wall tissues of the first and second nasal passages,
   b) an intermediate segment interconnecting the first and second end regions, and configured to traverse the bridge of the nose located between the first and second nasal passages,
   c) resilient means extending along the truss member, including a resilient spring member secured to at least a portion of the first and second end regions and the intermediate segment, the resilient spring member having upper and lower web members extending vertically from the intermediate segment of the resilient spring member and terminating at the intermediate segment of the truss member,
   d) adhesive means at the first and second end regions and the intermediate segment for removably engaging the dilator to the nose of a wearer, and
   e) a flexible cover member having one side secured to one side of the resilient spring member and extending outwardly beyond at least portions of the resilient spring member.

14. The nasal dilator of claim 13 including a flexible base layer having one side secured to the side of the resilient spring member opposite the side secured to the at least a portion of the first and second end regions.

15. The nasal dilator of claim 13 wherein at least one component of the truss member has at least portions of its end edges angled inward from bottom to top in a continous line, corresponding to a line where the nose meets the cheek.

16. The nasal dilator of claim 13 wherein the resilient spring member is bifurcated laterally to form resilient spring fingers extending into the first and second end regions of the truss member.

17. The nasal dilator of claim 13 including means at the intermediate segment midway between the first and second end regions of the truss members for alignment with the bridge of the nose of a wearer for centering the dilator across the nose.

18. A nasal dilator comprising a truss member, including:
   a) first and second end regions adapted to engage the outer wall tissues of the first and second nasal passages,
   b) an intermediate segment interconnecting the first and second end regions, and configured to traverse the bridge of the nose located between the first and second nasal passages,
   c) resilient means extending along the truss member, including a resilient spring member secured to at least a portion of the first and second end regions and the intermediate segment, said spring member being bifurcated laterally to form resilient spring fingers extending into the first and second end regions of the truss member,
   d) adhesive means at the first and second end regions and the intermediate segment for removably engaging the dilator to the nose of a wearer, and
   e) a flexible cover member having one side secured to one side of the resilient spring member and extending outwardly beyond at least portions of the resilient spring member.

19. The nasal dilator of claim 18 including a flexible base layer having one side secured to the side of the resilient spring member opposite the side secured to the at least a portion of the first and second end regions.

20. The nasal dilator of claim 18 wherein at least one component of the truss member has at least portions of its end edges angled inward from bottom to top in a continuous line, corresponding to a line where the nose meets the cheek.

21. The nasal dilator of claim 18 including indicator means at the intermediate segment midway between the first and second end regions of the truss member, for alignment with the bridge of the nose of a wearer for centering the dilator across the nose.

22. A nasal dilator comprising a truss member of different length, including:
   a) first and second end regions adapted to engage the outer wall tissues of the first and second nasal passages,
   b) an intermediate segment interconnecting the first and second end regions, and configured to traverse the bridge of the nose located between the first and second nasal passages,
   c) resilient means extending along the truss member, including a pair of parallel, spaced apart resilient spring members secured to at least a portion of the first and second end regions and the intermediate segment, d) adhesive means at the first and second end regions and the intermediate segment for removably engaging the dilator to the nose of a wearer, and, e) a flexible cover member having one side secured to one side of the resilient spring member and extending outwardly beyond at least portions of the resilient spring members.

23. The nasal dilator of claim 22 including a pair of notches extending inward from the opposite end edges of the truss member, and registering with and extending into the space between said resilient spring members.

24. The nasal dilator of claim 22 including at least one flexible base layer having one side secured to the side of said resilient spring member opposite the side secured to the at least a portion of the first and second end regions.

25. The nasal dilator of claim 22 including three tab extensions on the cover member projecting beyond the outer ends of the resilient spring members, the intermediate tab extension at each end of the spring members defining the spaced apart relationship of said spring members.

26. The nasal dilator of claim 25 wherein said three tab extensions have terminal end edges angled inward from bottom to top in a continuous line corresponding to a line where the nose meets the cheek.

27. The nasal dilator of claim 22 including indicator means at the intermediate segment midway between the first and second end regions of the truss member for alignment with the bridge of the nose of a wearer for centering the dilator across the nose.

28. A nasal dilator comprising a truss member, including:

a) first and second end regions adapted to engage the outer wall tissues of the first and second nasal passages, b) an intermediate segment interconnecting the first and second end regions, and configured to traverse the bridge of the nose located between the first and second nasal passages, c) resilient means extending along the truss member, including,
a resilient spring member secured to at least a portion of the first and second end regions and the intermediate segment, the resilient spring member including multiple resilient spring fingers diverging from a common center, d) adhesive means at the first and second end regions and the intermediate segment for removably engaging the dilator to the nose of a wearer, and e) a flexible cover member having one side secured to one side of the resilient spring member and extending outwardly beyond at least portions of the resilient spring member.

29. The nasal dilator of claim 28 including a flexible base layer having one side secured to the side of the resilient spring member opposite the side secured to the at least a portion of the first and second end regions.

30. The nasal dilator of claim 28 wherein the resilient spring fingers are further separated by slits extending substantially into the intermediate segment of the spring member.

31. The nasal dilator of claim 28 wherein the cover member includes a separation extending inward from each lateral end edge, said separation defining end portions of the cover member which register with corresponding resilient spring fingers.

32. The nasal dilator of claim 28 including indicator means at the intermediate segment midway between the first and second end regions of the truss member for alignment with the bridge of the nose of a wearer for centering the dilator across the nose.

33. The method of making a nasal dilator, comprising:

a) forming a plurality of spring members from an elongated sheet of synthetic resin, said spring members interconnected by webs located midway between their longitudinal ends, b) securing one side of the interconnected spring members to an elongated flexible cover material, and c) cutting through at least the cover material on a predetermined line which extends around at least portions of each interconnected spring member.

34. The method of claim 33 wherein the elongated sheet of synthetic resin includes an elongated flexible base layer material.

35. The method of claim 33 including securing the side of the interconnected spring members opposite the side secured to the cover material to an elongated flexible base layer material.

36. The method of claim 33 wherein said cutting includes a separation of material midway between the longitudinal ends of each spring member.

37. The method of claim 33 wherein said cutting severs said webs substantially where said webs connect to each spring member.

38. The method of claim 33 wherein said cutting severs said webs substantially beyond where said webs connect to each spring member.

39. The method of claim 33 wherein the cutting forms angled end edges which correspond to a line where the nose meets the cheek of a wearer.

40. The method of claim 33 wherein said cutting includes the formation of indicator means at the intermediate segment midway between the first and second end regions of the truss member for alignment with the bridge of the nose of a wearer for centering the dilator across the nose.

* * * * *

UNITED STATES PATENT AND TRADEMARK OFFICE
CERTIFICATE OF CORRECTION

PATENT NO. : 6,453,901 B1 Page 1 of 1
DATED : September 24, 2002
INVENTOR(S) : Joseph V. Ierulli It is certified that error appears in the above-identified patent and that said Letters Patent is hereby corrected as shown below:

<u>Column 11,</u>
Line 13, should read:
-- bridge of the nose located between the first and second nasal passages, --.

Signed and Sealed this

Third Day of December, 2002

JAMES E. ROGAN
*Director of the United States Patent and Trademark Office*